(12) United States Patent
Chan et al.

(10) Patent No.: US 9,643,031 B2
(45) Date of Patent: May 9, 2017

(54) DISPERSIBLE CATIONIC POLYGALACTOMANNAN POLYMERS FOR USE IN PERSONAL CARE AND HOUSEHOLD CARE APPLICATIONS

(75) Inventors: Anita N. Chan, Wilmington, DE (US); Paquita Erazo-Majewicz, Landenberg, PA (US); Gijsbert Kroon, Giessendam (NL); Thomas G. Majewicz, Landenberg, PA (US)

(73) Assignee: HERCULES LLC, Wilmington, DE (US)

( * ) Notice: Subject to any disclaimer, the term of this patent is extended or adjusted under 35 U.S.C. 154(b) by 1396 days.

(21) Appl. No.: 11/982,591

(22) Filed: Nov. 2, 2007

(65) Prior Publication Data
US 2008/0112907 A1   May 15, 2008

Related U.S. Application Data

(60) Provisional application No. 60/856,486, filed on Nov. 3, 2006.

(51) Int. Cl.
| | | |
|---|---|---|
| A61K 8/02 | (2006.01) | |
| A61K 8/73 | (2006.01) | |
| A61Q 5/02 | (2006.01) | |
| C08B 37/00 | (2006.01) | |
| A61Q 5/12 | (2006.01) | |
| A61Q 19/10 | (2006.01) | |
| C11D 3/22 | (2006.01) | |

(52) U.S. Cl.
CPC .............. *A61Q 5/02* (2013.01); *A61K 8/0241* (2013.01); *A61K 8/737* (2013.01); *A61Q 5/12* (2013.01); *A61Q 19/10* (2013.01); *C08B 37/0096* (2013.01); *C11D 3/227* (2013.01); *A61K 2800/48* (2013.01); *A61K 2800/5426* (2013.01)

(58) Field of Classification Search
None
See application file for complete search history.

(56) References Cited

U.S. PATENT DOCUMENTS

| | | | |
|---|---|---|---|
| 3,808,195 A | 4/1974 | Shelso et al. | 260/209 R |
| 4,363,669 A | 12/1982 | Cottrell et al. | 106/205 |
| 4,645,833 A | 2/1987 | Bayerlein | 536/17.1 |
| 4,654,158 A | 3/1987 | Shepherd, Jr. | 252/91 |
| 4,659,811 A | 4/1987 | Wu | 536/114 |
| 4,677,201 A | 6/1987 | Morgan | 536/114 |
| 4,959,464 A * | 9/1990 | Yeh | 536/114 |
| 5,104,436 A | 4/1992 | Lauderdale | 71/27 |
| 5,186,928 A * | 2/1993 | Birtwistle | 424/70.9 |
| 5,536,825 A | 7/1996 | Yeh et al. | 536/52 |
| 5,670,141 A | 9/1997 | Nehra | 424/61 |
| 6,930,078 B2 * | 8/2005 | Wells et al. | 510/121 |
| 2005/0026794 A1 * | 2/2005 | Utz et al. | 510/130 |
| 2005/0227902 A1 | 10/2005 | Erazo-Majewicz et al. | 510/470 |

FOREIGN PATENT DOCUMENTS

| | | | | |
|---|---|---|---|---|
| CA | 2063365 A1 | 4/1993 | | |
| EP | 0568235 A | 3/1994 | | A61K 7/32 |
| FR | 2513265 A | 3/1983 | | C13L 3/00 |
| WO | WO 03 078474 A1 | 9/2003 | | C08B 37/00 |
| WO | WO 2004 065433 A1 | 8/2004 | | C08F 18/08 |
| WO | WO 2006 106366 A | 10/2006 | | A61Q 5/12 |

OTHER PUBLICATIONS

"N-Hance® Cationic Guar and AquaCat® Cationic Guar Solutions" [online], [retrieved Sep. 21, 2010]. Retrieved from the internet <http://www.essentialingredients.com/pdf/Cationic%20Guar%20Personal%20Care%20brochure.pdf>.*

Chiron, S. (2004) Performance and Sensorial Benefits of Cationic Guar in Hair Care Applications. Cosmetics & Toiletries, vol. 119, No. 2, p. 47-52.*

Irit Gliko-Kabir, et al. Phosphated crosslinked guar for colon-specific drug delivery II. In vitro and in vivo evaluation in the rate, Journal of Controlled Release, 2000, p. 129-134, vol. 63, Elsevier, The Netherlands.

* cited by examiner

*Primary Examiner* — Leigh C Maier
(74) *Attorney, Agent, or Firm* — Dunlap Codding, P.C.; Shaorong Chen

(57) ABSTRACT

The present invention relates to polygalactomannan compositions, and more particularly cationic guar gum compositions, which, when crosslinked with glyoxal, from discrete guar particles which are capable of being easily dispersed in water which permits subsequent processing of the guar, such as washing. The guar and its derivatives are desirable for use in applications such as personal care, household care products and the like.

7 Claims, 2 Drawing Sheets

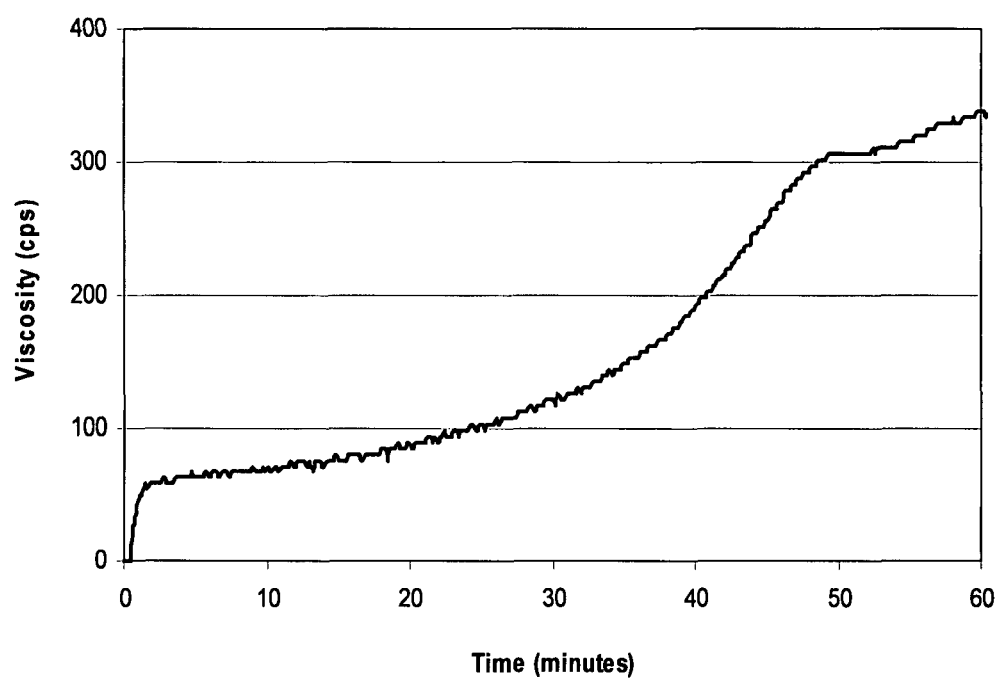
Figure 1. Dispersion of Example 2
1% Product in Distilled Water

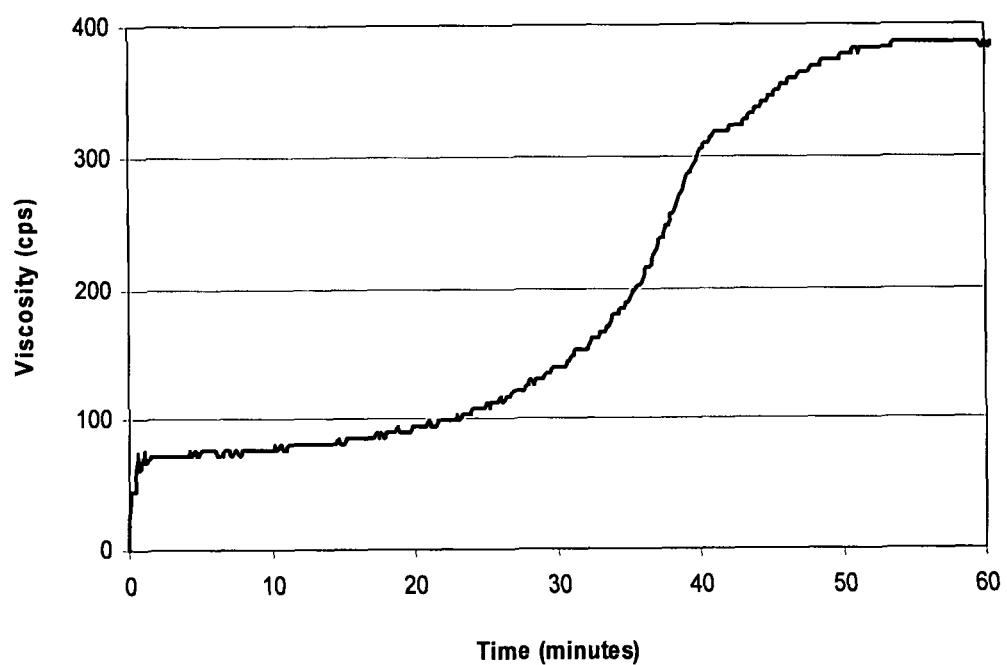
Figure 2. Dispersion of Example 3
1% Product in Distilled Water

DISPERSIBLE CATIONIC POLYGALACTOMANNAN POLYMERS FOR USE IN PERSONAL CARE AND HOUSEHOLD CARE APPLICATIONS

RELATED APPLICATIONS

This application claims the benefit of U.S. Provisional Application Ser. No. 60/856,486, filed on Nov. 3, 2006, which is incorporated herein by reference in its entirety.

FIELD OF THE INVENTION

The present invention relates to polygalactomannan compositions and more particularly guar gum compositions which, when crosslinked with glyoxal, from discrete guar particles which are capable of being easily dispersed in water which permits subsequent processing of the guar, such as washing. The guar and its derivatives are desirable for use in applications such as personal care or household care products, and the like.

BACKGROUND OF THE INVENTION

Polygalactomannans and their derivatives are used in various applications such as oil recovery, personal care products, textile applications, paper applications, coating applications, food applications, etc. Polygalactomannans and their derivatives are difficult to disperse in aqueous solutions, as they tend to form sticky particles which clump and agglomerate, making dissolution difficult. To improve dissolution of the polymers, crosslinking agents, such as borax, are used to allow for water-washing of the polygalactomannan after reaction and for improved dispersibility of the polygalactomannan in water.

Crosslinking agents based on borate salts, aluminum salts, copper, iron, lead, calcium, and sodium salts have been described. Other crosslinking agents such as metal salts based on titanium and zirconium have been mentioned, without clear definition of the method or procedure for their use.

There exists a concern over the hazards of boron containing compounds in some consumer products, and a need exists for alternative crosslinking agents for use in the purification and handling of polygalactomannan polymers and their derivatives.

In personal care applications, such as in hair care and skincare, and in household care applications, such as fabric care applications, there is a desire to deposit a coating produced without the use of boron containing compounds onto the substrate. In the case of hair care applications, the resultant deposited coating reduces the energy needed to move a comb through hair in the wet or dry state or delivers a silky, soft feel to skin or to fabric. This coating can also act to improve the luster and moisture retention of hair and skin, as well as their manageability and feel.

SUMMARY OF THE INVENTION

In a first aspect, the present invention relates to a process for producing a polygalactomannan comprising the steps of: obtaining a cationic polygalactomannan; crosslinking the polygalactomannan with an effective amount of glyoxal to produce a crosslinked cationic polygalactomannan particle. The crosslinked cationic polygalactomannan particle is subsequently dispersed in water having a pH in the range of from below about 7 to about 3 and washed in water to remove impurities from the crosslinked cationic polygalactomannan particle.

In a second aspect, the present invention is directed to a personal care or home care composition comprising a glyoxal crosslinked cationic polygalactomannan polymer and derivatives. This gyloxal crosslinked cationic polygalactomannan is of utility in various applications such as personal care products or home care products. The gyloxal crosslinked cationic polygalactomannan is of particular utility in applications where the use of boron containing compounds are to be reduced or eliminated.

BRIEF DESCRIPTION OF THE DRAWINGS

FIG. 1 is a graph of the viscosity of a 1% dispersion of the product of Example 2 in distilled water over time at a pH of ?.

FIG. 2 is a graph of the viscosity of a 1% dispersion of the product of Example 3 in distilled water over time.

DETAILED DESCRIPTION OF THE INVENTION

In the present invention, it has been found that treatment of a cationic polygalactomannan reaction mixture with glyoxal at a ratio of between about 0.5-5.0 wt glyoxal/wt galactomannan polymer leads to a water-dispersible polygalactomannan that remains as a discrete particulate that does not agglomerate into a gel. The resulting product is easily washed in water and readily dispersible in water.

This application is of utility as a processing aid for galactomannans. Polygalactomannans are polysaccharides composed principally of galactose and mannose units and are usually found in the endosperm of leguminous seeds such as guar, locust bean, honey locust, flame tree, and the like. The polygalactomannans may be used in either their natural form or may be substituted with one or more functional groups (e.g., carboxymethyl group). The most commonly used polygalactomannan is guar. The guar is a derivatized guar, namely cationic guar.

An advantage of the use of glyoxal over borate salts is that borate crosslinked polygalactomannans disassociate more rapidly in water at an acidic pH than glyoxal treated galactomannans. This results in the formation of swelled gel particles or a gel mass at an acidic pH. By permitting the polygalactomannan to remain as a discrete particle at lower pH values, washing of the polygalactomannan over a greater pH range may be performed and thereby permitting removal of impurities that would not be removed at the higher pH ranges. These impurities may reduce the clarity of aqueous solutions of the polygalactomannan or be harmful if permitted to remain with the galactomannan in certain end use applications, such as personal care.

In addition, it has been found that glyoxal treated cationic polygalactomannans function well as conditioning agents and thickening agents in personal care compositions.

In accordance with the present invention, the cationic polygalactomannan or derivative thereof generally has a substituent degree of substitution (DS) lower limit of about 0.001 and an upper limit of about 3.0. Preferably, the lower limit of the cationic DS is 0.01, and more preferably 0.05. Preferably, the upper limit of the cationic DS is 3.0, more preferably 1.0, and even more preferably 0.25. The cationic polygalactomannan or derivative thereof of the present invention generally has a weight average molecular weight (Mw) with a lower limit of about 50,000 and an upper limit of about 5,000,000 preferably, the lower limit of the molecular weight is 300,000, and more preferably 400,000. Preferably, the upper limit of the molecular weight is 1,500,000, more preferably 1,000,000.

The cationic functionality of the polygalactomannan or derivatized polygalactomannan can be added to the backbone by known methods. For example, the polygalactomannan material can be reacted for a sufficient time and at a sufficient temperature with tertiary amino or quaternary ammonium alkylating reagents, such 2-dialkylaminoethyl chloride and quaternary ammonium compounds such as 3-chloro-2-hydroxypropyltrimethylammonium chloride, and 2,3-epoxy-propyltrimethylammonium chloride. Preferred examples include glycidyltrialkylammonium salts and 3-halo-2-hydroxypropyltrialkylammonium salts such as glycidyltrimethylammonium chloride, glycidyltriethylammonium chloride, gylcidyltripropylammonium chloride, glycidylethyldimethylammonium chloride, glycidyidiethylmethylammonium chloride, and their corresponding iodides; 3-chloro-2-hydroxypropyltrimethylammonium chloride, 3-chloro-2-hydroxypropyltriethylammonium chloride, 3-chloro-2-hydroxypropyltripropylammonium chloride, 3-chloro-2-hydroxypropylethyldimethylammonium chloride, and their corresponding iodides; and quaternary ammonium compounds such as halides of imidazoline ring containing compounds.

The cationic polygalactomannan may also contain other substituent groups such as nonionic substituents, i.e., alkyl or hydroxyalkyl wherein the alkyl represents an aromatic, straight or branched hydrocarbon moiety having 1 to 30 carbon atoms (e.g., ethyl or hydroxyethyl, propyl or hydroxypropyl, butyl or hydroxybutyl) or anionic substituents, such as carboxymethyl groups are optional. These optional substituents are linked to the polygalactomannan polymer by the reaction with reagents such as (1) alkylene oxides (e.g., ethylene oxide, propylene oxide, butylene oxide) to obtain hydroxyethyl groups, hydroxypropyl groups, or hydroxybutyl groups, or with (2) chloromethyl acetic acid to obtain a carboxymethyl group. The process for preparing derivatized polygalactomannan is well known in the art. The cationic polygalactomannan may also contain mixture of one or more other substituent groups such as nonionic, anionic and cationic substituents.

Cationic polygalactomannan polymers or their derivatives, useful in the invention can be treated with several known reagents, such as (1) caustic, (2) acids, (3) by biochemical oxidants, such as galactose oxidase, (4) chemical oxidants, such as hydrogen peroxide, (5) a physical method using high speed agitation and shearing machines, (6) thermal methods, (7) enzymatic reagents, and (8) mixtures of these reagents and methods. Reagents such as sodium metabisulfite or inorganic salts of bisulfite may also be optionally included.

The preferred end-use of the glyoxal treated cationic polygalactomannan polymers of the invention is as a component in personal care compositions or household care compositions, where the composition comprises a glyoxal treated cationic polygalactomannan and an active ingredient. The active ingredient includes, but is not limited to, personal care active ingredients, such as for example, analgesics, anesthetics, antibiotic agents, antifungal agents, antiseptic agents, antidandruff agents, antibacterial agents, vitamins, hormones, antidiarrhea agents, corticosteroids, anti-inflammatory agents, vasodilators, kerolytic agents, dry-eye compositions, wound-healing agents, anti-infection agents, as well as solvents, diluents, adjuvants and other ingredients such as water, ethyl alcohol, isopropyl alcohol, propylene glycol, higher alcohols, glycerine, sorbitol, mineral oil, preservatives, surfactants, propellants, fragrances, essential oils, and viscosifying agents.

In accordance with the present invention, the personal care active ingredient should provide some benefit to the user's body. Personal care compositions include hair care, skincare, sun care, and oral care compositions. Examples of personal care ingredients that may suitably be included, but not limited to, in the personal care products according to the present invention are as follows:

1) Perfumes, which give rise to an olfactory response in the form of a fragrance and deodorant perfumes which in addition to providing a fragrance response can also reduce body malodor;

2) Skin coolants, such as menthol, menthyl acetate, menthyl pyrrolidone carboxylate N-ethyl-p-menthane-3-carboxamide and other derivatives of menthol, which give rise to a tactile response in the form of a cooling sensation on the skin;

3) Emollients, such as isopropylmyristate, silicone materials, mineral oils and vegetable oils which give rise to a tactile response in the form of an increase in skin lubricity;

4) Deodorants other than perfumes, whose function is to reduce the level of or eliminate micro flora at the skin surface, especially those responsible for the development of body malodor. Precursors of deodorants other than perfume can also be used;

5) Antiperspirant actives, whose function is to reduce or eliminate the appearance of perspiration at the skin surface;

6) Moisturizing agents, that keep the skin moist by either adding moisture or preventing from evaporating from the skin;

7) Cleansing agents, that remove dirt and oil from the skin;

8) Sunscreen active ingredients, that protect the skin and hair from UV and other harmful light rays from the sun. In accordance with this invention a therapeutically effective amount will normally be from 0.01 to 10% by weight, preferable 0.1 to 5% by weight of the composition;

9) Hair treatment agents, that condition the hair, cleanse the hair, detangles hair, acts as styling agent, volumizing and gloss agents, color retention agent, antidandruff agent, hair growth promoters, hair dyes and pigments, hair perfumes, hair relaxer, hair bleaching agent, hair moisturizer, hair oil treatment agent, and antifrizzing agent;

10) Oral care agents, such as dentifrices and mouth washes, that clean, whiten, deodorize and protect the teeth and gum;

11) Denture adhesives that provide adhesion properties to dentures;

12) Shaving products, such as creams, gels and lotions and razor blade lubricating strips;

13) Pigments or dyes that impart color to the hair, skin, or textile substrate.

In accordance with the present invention, the household care active ingredient should provide some benefit to the user. Examples of household care ingredients that may suitably be included, but not limited to, according to the present invention are as follows:

1) Perfumes, which give rise to an olfactory response in the form of a fragrance and deodorant perfumes which in addition to providing a fragrance response can also reduce odor;

2) Insect repellent agent whose function is to keep insects from a particular area or attacking skin;

3) Bubble generating agent, such as surfactant that generates foam or lather;

4) Pet deodorizer or insecticides such as pyrethrins that reduces pet odor;

5) Pet shampoo agents and actives, whose function is to remove dirt, foreign material and germs from the skin and hair surfaces;

6) Industrial grade bar, shower gel, and liquid soap actives that remove germs, dirt, grease and oil from skin, sanitizes skin, and conditions the skin;

7) All purpose cleaning agents, that remove dirt, oil, grease, germs from the surface in areas such as kitchens, bathroom, public facilities;

8) Disinfecting ingredients that kill or prevent growth of germs in a house or public facility;

9) Rug and Upholstery cleaning actives which lift and remove dirt and foreign particles from the surfaces and also deliver softening and perfumes;

10) A laundry softener active, which reduces static and makes fabric feel softer;

11) Laundry detergent ingredients which remove dirt, oil, grease, stains and kills germs;

12) Laundry or detergent or fabric softener ingredients that reduce color loss during the wash, rinse, and drying cycle of fabric care;

13) Dishwashing detergents which remove stains, food, germs;

14) Toilet bowl cleaning agents, which remove stains, kills germs, and deodorizes;

15) Laundry prespotter actives which helps in removing stains from clothes;

16) Fabric sizing agent which enhances appearance of the fabric;

17) Vehicle cleaning actives which removes dirt, grease, etc. . . . from vehicles and equipment;

18) Lubricating agent which reduces friction between parts; and

The above list of personal care and household care active ingredients are only examples and are not a complete list of active ingredients that can be used. Other ingredients that are used in these types of products are well known in the industry. In addition to the above ingredients conventionally used, the composition according to the present invention can optionally also include, but is not limited to, ingredients such as a colorant, preservative, antioxidant, nutritional supplements, alpha or beta hydroxy acid, activity enhancer, emulsifiers, functional polymers, viscosifying agents (such as salts, i.e., NaCl, NH$_4$Cl & KCl, water-soluble polymers, i.e., hydroxyethylcellulose, hydroxypropylmethylcellulose, and fatty alcohols, i.e., cetyl alcohol), alcohols having 1-6 carbons, fats or fatty compounds, antimicrobial compound, zinc pyrithione, silicone material, hydrocarbon polymer, emollients, oils, surfactants, medicaments, flavors, fragrances, suspending agents, and mixtures thereof.

In accordance with the present invention, examples of functional polymers that can be used in blends with the glyoxal treated polygalactomannan or derivatives thereof of this invention include water-soluble polymers such as acrylic acid homopolymers such as Carbopol® product and anionic and amphoteric acrylic acid copolymers, vinylpyrrolidone homopolymers and cationic vinylpyrrolidone copolymers; nonionic, cationic, anionic, and amphoteric cellulosic polymers such as hydroxyethylcellulose, hydroxypropylcellulose, carboxymethylcellulose, hydroxypropylmethylcellulose, cationic hydroxyethylcellulose, cationic carboxymethylhydroxyethylcellulose, and cationic hydroxypropylcellulose; acrylamide homopolymers and cationic, amphoteric, and hydrophobic acrylamide copolymers, polyethylene glycol polymers and copolymers, hydrophobic polyethers, hydrophobic polyetheracetals, hydrophobically-modified polyetherurethanes and other polymers referred to as associative polymers, hydrophobic cellulosic polymers, polyethyleneoxide-propylene oxide copolymers, and nonionic, anionic, hydrophobic, amphoteric, and cationic polysaccharides such as xanthan, chitosan, carboxymethyl, alginates, and gum arabic.

In accordance with the invention, the silicone materials which can be used are polyorganosiloxanes that can be in the form of polymers, oligomers, oils, waxes, resins, or gums or polyorganosiloxane polyether copolyols, amodimethicones, cationic polydimethylsiloxane materials and any other silicone material that is used in personal care or household care compositions.

In one embodiment, the hair care or skin care composition of the present invention is an aqueous system comprising water and the polymer of the invention. In one embodiment, the hair care or skin care composition of the present invention contains one or more surfactant compounds, including amphoteric surfactants, cationic surfactants, anionic surfactants, nonionic surfactants, zwitterionic surfactants, and combinations thereof.

It has been found that glyoxal treated cationic polygalactomannans can deposit with high efficacy on hair/skin and can impart conditioning benefits to the discussed keratin substrates.

Such polymers impart other benefits in hair styling, body lotions and sunscreens due to hydrophobic film formation on keratin substrates that would act as barrier between the these surfaces and the surrounding atmosphere.

The polymers of this invention can be useful as conditioning agents in 2-in-1 shampoos, body lotions, sunscreens, anti-frizz and hair styling. The polymers of this invention can also be used to improve hair volume, manageability, hair repair, or color retention, skin moisturization and moisture retention, fragrance retention, sunscreen longevity on hair, skin, and fabrics, flavor enhancement and antimicrobial performance in oral care applications, and improve fabric abrasion resistance and colorfastness in household care applications.

Wet and dry hair combability measurements are typical test methods used to measure conditioning performance in shampoo and conditioner applications. In skincare applications, skin lubricity or reduced friction or softer feel of the skin, reduced water vapor transmission and improved skin elasticity are test methods used to measure skin conditioning. In surfactant-based household cleansing product formulations where conditioning performance is desired, such as dish detergents, fabric softeners, and antistatic products, conditioning refers to imparting a softer feel to fabric and eliminating static effects, eliminating fabric fiber breakage or deformation known as pilling. Imparting color retention properties to fabrics is also important and can be measured.

The following examples demonstrate the crosslinking of cationic guar with glyoxal and their use in personal care compositions. The examples are merely set forth for illustrative purposes all parts and percentages being by weight, unless otherwise indicated. It is to be understood that other modifications of the present invention can be made by skilled artisans in the related industry without departing from the spirit and scope of the invention.

COMPARATIVE EXAMPLE 1 AND EXAMPLES 2-4

Cationic Guar Preparation

Cationic guar was prepared by known procedures, without the use of a crosslinking agent.

Guar splits (882 g), and water (450 g) were mixed in a stirred reactor under nitrogen. The reactor is purged with nitrogen and vented to remove oxygen. The reaction is conducted at a temperature between 30-50° C., after addition of 3-chloro-2hydroxypropyltrimethylammonium chloride (289 g of a 65% aqueous solution), followed by 280 grams of 25% sodium hydroxide. The reaction is cooled to room temperature.

When the cationic guar splits were washed with water to remove salts and impurities, the splits turned into swollen gel, and filtration was not possible. A sample of the non-purified splits was dried and ground to determine the salts content, analyzed as sulfate ash. The reaction product is shown in Comparative Example 1 in Table 1.

Glyoxal Crosslinking

A cationic guar was prepared similarly to Example 1. At the end of the reaction with 3-chloro-2hydroxypropyltrim-ethylammonium chloride, various amounts of Acetic Acid and Glyoxal were added with stirring. The amounts of Acetic Acid and Glyoxal used are indicated in Table 1 for Examples 2-4. The mixture was heated to above 45° C. to effect crosslinking.

Wash Procedure

After the reaction mixture was cooled to ambient temperature, the crude product was washed with water for 2 hours. The product was then filtered, dried and ground.

The residual salts as a result of the water purification are shown in Table 1.

TABLE 1

Crosslinking of Cationic Guar

| | Example | | | |
|---|---|---|---|---|
| | 1 (Comparative Example) | 2 | 3 | 4 |
| Acetic Acid, g | 0 | 225 | 135 | 90 |
| 40% Glyoxal Solution, g | 0 | 28 | 56 | 16 |
| Water Wash Filtration | 2 hours no free liquid | 2 hours filtered well | 2 hours filtered well | 40 minutes filtered well |
| Cat DS | ~0.14 | 0.14 | 0.14 | 0.11 |
| Ash,% | 11 | 2 | 2 | 3 |
| Dispersibility of 1% Product in Water | — | dispersed well | dispersed well | dispersed well |

The final product was analyzed to have a degree of cationic substitution of 0.14 for both Examples 2 and 3 and 0.11 for Example 4. Comparative Example 1 is presumed to have the same DS as the same recipe was used for the cationic derivatization.

Aside from enabling water purification, the glyoxal crosslinking also provides a water-dispersible product. The non-crosslinked product clumped readily when added to water. FIGS. 1 and 2 illustrate that the products produced in Examples 2 and 3 were easily dispersed in water before they started to dissolve.

EXAMPLES 5 AND 6 AND COMPARATIVE EXAMPLE 7

Additional crosslinked products of the invention are shown in Examples 5 and 6 in Table 2. Example 5 was prepared according to the procedure in Example 3 to produce a cationic guar with a cationic DS of 0.14. The product in Example 6 was prepared according to the procedure in Example 3, using a 30% greater amount of 2-hydroxypropyl-3-trimethylammonium chloride to achieve a cationic DS of 0.2. A 1% aqueous viscosity of the products of the invention in Examples 5 and 6 are similar to the 1% aqueous viscosity of the comparative borate crosslinked cationic guar in Example 7.

EXAMPLE 8 AND 9 AND COMPARATIVE EXAMPLES 10-11

Demonstration of Conditioning Performance of Products of the Invention

The use of the cationic polygalactomannan materials of the invention of Examples 5 and 6 in a conditioning shampoo formulation is demonstrated in Examples 8 and 9, Table 2, and contrasted with a comparative control shampoo containing the borate crosslinked cationic guar of Example 7(Example 10) and a shampoo containing no cationic guar (Example 11).

Shampoo Preparation

The conditioning shampoo formulations in Table 2 were prepared by combining 77 parts by weight (pbw) of the surfactant premix composition shown in Table 3 with 19 pbw deionized water, and 0.3 pbw of the polymer of the invention using a Caframo overhead mechanical stirrer with a dispersion blade, stirring at 600 rpm, and allowing the composition to mix for 45 minutes at ambient temperature. At this time, 3 pbw of a silicone emulsion (Dow Corning 1784) was added to the formulation, and mixing was continued for an additional 15 minutes. The shampoo compositions were maintained at ambient temperature overnight, and the viscosity of each shampoo was measured using a Brookfield LVT viscometer with a small sample adapter, spindle 31, at the specified rotation speed.

Shampoo Viscosity Measurements

Comparison of the shampoo viscosity for Examples 8 and 9, which contain the glyoxal crosslinked cationic guars of the invention, with comparative Example 11, which contains no polymer, demonstrates the viscosifying performance of the products of the invention. The viscosities of the shampoos in Examples 8 and 9 are similar to the viscosity of the shampoo containing borate crosslinked cationic guar in Example 10.

Cationic polysaccharides and other polymers have been used widely in personal care, household care, industrial, and institutional products to perform a function in the final product, ranging from the use of the polymer as gellants, binders, thickeners, stabilizers, emulsifiers, spreading and deposition aids and carriers for enhancing the rheology, efficacy, deposition, aesthetic and delivery of chemically and physiologically active ingredients in personal care, household care, institutional and industrial compositions. Depending on the application, the substrate to which the product is applied can be skin, hair, or textile substrate.

Cationic polysaccharides are used in hair care products to provide conditioning to the hair. In skin care products, these same polymers can provide conditioning effects to the skin. When incorporated into detergent and fabric softening formulations, these same polymers can provide conditioning, softening, anti-abrasion and antistatic characteristics to fabrics.

Wet and dry combability measurements are typical test methods used to measure conditioning performance in shampoo and conditioner applications. The combing performance of each shampoo formulation was measured within 24 hours of shampoo preparation, on two medium brown virgin European hair tresses (National Hair Importers, New Jersey) that had been previously treated with a solution of sodium lauryl sulfate (SLS), rinsed, and dried overnite at 23° C. and 50% relative humidity.

Combing Performance Measurements

Combing performance was measured by applying the shampoo formulation to a tress wet with water, at a ratio of 0.5 pbw shampoo/1 pbw hair tress. The tress was kneaded for 60 seconds, then rinsed with 40° C. water for 30 seconds. This process was repeated, then the tress was rinsed with deionized water and excess water squeezed from the tress. The tress was placed on the double comb apparatus and wet combing force measured 8 times on an Instron 5542 at a cross head speed of 12.5 cm/min using the double comb method, with Ace hard rubber fine pocket combs, at 23° C. and 50% relative humidity. Hair tresses were then allowed to dry overnight at 23° C. and 50% relative humidity, and the dry comb performance was measured using the same double comb method. The normalized comb energies in Table 2 represent the total comb energy/weight of tress.

The conditioning performance of the products of the invention is demonstrated by the significantly reduced wet and dry combing energy results for Examples 8 and 9 compared to the corresponding higher combing energies for the no polymer control shampoo in Example 11. The combing energies for Examples 8 and 9 compare well with the comb energy for the shampoo containing borate crosslinked cationic guar in Example 10.

TABLE 2

Glyoxal Crosslinked Cationic Galactomannan Polymers Performance in Conditioning Shampoo

| | Example | | |
|---|---|---|---|
| | 5 | 6 | 7(Comparative Example)[1] |
| Treatment | glyoxal | glyoxal | Borate |
| Cationic DS | 0.14 | 0.256 | 0.13 |
| % Moisture | 7.8 | 7.3 | |
| Aqueous Viscosity @ 1% as received, cps. | 2650 | 2600 | 3500 |

| | Example | | | |
|---|---|---|---|---|
| | 8 | 9 | 10(comparative example) | 11(Comparative Example-No Polymer) |
| Conditioning Shampoo viscosity (Brookfield LVT sp. #31, small sample adapter, 6 rpm, pH 5.1), cps. | 4855 | 5780 | 6010(3 rpm; pH 5.8) | 1421(12 rpm) |
| Normalized Wet Comb Energy (gf-mm/g) | 1262 | 1345 | 963 | 2340 |
| Normalized Dry Comb Energy (gf-mm/g) | 301 | 281 | 242 | 670 |

[1]N-Hance ® 3196 cationic guar, borate crosslinked (Aqualon Division of Hercules Incorporated)

TABLE 3

Shampoo Premix Composition

| Ingredient | manufacturer | Parts by weight |
|---|---|---|
| Deionized water | | 896 |
| Stepanol AM | Stepan | 1027 |
| Steol CA-330 | | 310 |
| Amphosol CA | | 186 |

TABLE 3-continued

Shampoo Premix Composition

| Ingredient | manufacturer | Parts by weight |
|---|---|---|
| Glydant | Lonza | 16.25 |
| 25 wt % Ammonium Chloride(aq) | | 65 |

EXAMPLES 12-13 AND COMPARATIVE EXAMPLE 14

Demonstration of Use in Skin Care Application, Bodywash

The thickening performance of the products of the invention in a bodywash formulation are demonstrated in Table 4. Bodywash formulations were prepared by addition of 0.3 pbw of the polymers of the invention in Examples 5 and 6 to 76 pbw of the bodywash premix formulation in Table 5, and water (added to bring the volume to 100). Mixing was performed using an overhead mechanical stirrer with a dispersion blade, for 1 hr. The pH of the bodywash was 5.6.

The bodywash examples 12 and 13 contain the polymers of the invention of Examples 5 and 6, respectively. Addition of the polymers of the invention to the bodywash formulation leads to increased viscosity of the bodywash relative to the comparative control bodywash, containing no cationic guar, in Example 14.

TABLE 4

Performance of Products of the Invention in Bodywash Formulation

| | Example | | |
|---|---|---|---|
| | 12 | 13 | 14 |
| Polymer | Ex. 5 | Ex. 6 | None |
| Viscosity/cps[1] | 5120 | 5020 | 1864 |

[1]Brookfield LVT, sp. 3, 12 rpm

TABLE 5

Bodywash Premix Formulation

| Ingredient | Manufacturer | Parts by weight |
|---|---|---|
| Stepanol AM | Stepan Chemical Co. | 697 |
| Steol CA 330 | | 2500 |
| Amphosol CA | | 500 |
| Deionized water | | 279 |
| Glydant | Lonza Chemicals | 24.5 |

In accordance with the present invention, the cationic, polygalactomannan or derivative thereof generally has a cationic degree of substitution (DS) lower limit of about 0.001 and an upper limit of about 3.0.

In addition to the use of glyoxal as a crosslinking agent for polygalactomannan polymers and their derivatives, other agents which form a water-swellable or water-dispersible complex with the polygalactomannan polymers, can also act to improve the water-dispersibility of the polygalactomannan. These agents include oligomers or polymers containing phosphate, sulfate, sulfonate, carboxylate, or carbonate groups, including sodium hexametaphosphate polystyrene sulfonate, and proteins such as casein or whey which can form a water-dispersible complex with cationic polygalactomannan polymers. These agents also include anionic, cationic, and amphoteric surface-active agents such as ammonium lauryl sulfate, sodium lauryl sulfate, cetyltrimethylammonium chloride or bromide, and cocamidopropyl betaine.

In addition, other crosslinkers, such as chloroformate, siloxane based crosslinking reagents, such as triethoxysilane, can be used to crosslink the polygalactomannan, rendering it water-dispersible.

The water-dispersible crosslinked products described above can then be used in applications such as oil recovery, personal care products, textile applications, paper applications, coating applications, food applications where they can be dispersed and dissolved in aqueous phases by appropriate adjustment of the solution pH or by addition of salts.

Although the invention has been described with referenced to preferred embodiments, it is to be understood that variations and modifications in form and detail thereof may be made without departing from the spirit and scope of the claimed invention. Such variations and modifications are to be considered within the purview and scope of the claims appended hereto.

What is claimed:

1. A personal care composition, comprising:
   (i) an active ingredient agent; and
   (ii) a purified glyoxal crosslinked cationic guar having a weight average molecular weight in a range of from about 400,000 to about 1,500,000 Daltons,
   wherein:
      (a) the purified glyoxal crosslinked cationic guar comprises glyoxal crosslinked cationic particles prepared by a process comprising the steps of:
         treating cationic guar splits with an effective amount of glyoxal to form glyoxal crosslinked cationic guar splits,
         dispersing the glyoxal crosslinked cationic guar splits in water having a pH from less than about 7 to about 3,
         washing the glyoxal crosslinked cationic guar splits in water,
         drying the glyoxal crosslinked cationic guar splits, and
         mechanically processing the glyoxal crosslinked cationic guar splits to form glyoxal crosslinked cationic guar particles; and
      (b) the personal care composition (I) has a pH in a range of from about 5.1 to about 5.6, and (II) is selected from the group consisting of cleansing compositions, conditioners, and hair styling products.

2. The composition of claim 1, wherein the purified glyoxal crosslinked cationic guar has a substituent degree of substitution (DS) in a range of from 0.001 to 3.0.

3. The composition of claim 1, wherein the personal care composition further comprises one or more surfactant compounds, selected from the group consisting of amphoteric surfactants, cationic surfactants, anionic surfactants, nonionic surfactants, zwitterionic surfactants, and combinations thereof.

4. The composition of claim 3, further comprising one or more additional ingredients selected from the group consisting of preservatives, thickeners, functional polymers, viscosity modifiers, electrolytes, pH adjusting agents, perfumes, dyes, UV screens, organosilicone materials, antidandruff agents, vitamins, and vitamin derivatives.

5. The composition of claim 1, wherein the personal care composition is a hair care composition.

6. The composition of claim 1, wherein the personal care composition is a skin care composition.

7. The composition of claim 1, wherein the purified glyoxal crosslinked cationic guar is present in the personal care composition at about 0.3% by weight.

* * * * *